US011359176B2

(12) United States Patent
Mohan et al.

(10) Patent No.: US 11,359,176 B2
(45) Date of Patent: Jun. 14, 2022

(54) MICROFLUIDIC DEVICE FOR CELL CULTURE MONITORING

(71) Applicant: Global Life Sciences Solutions USA LLC, Marlborough, MA (US)

(72) Inventors: Prashanth Hosabettu Mohan, Bangalore Karnataka (IN); Sandip Maity, Bangalore Karnataka (IN); Nagapriya Kavoori Sethumadhavan, Bangalore Karnataka (IN); Swapnil Puranik, Bangalore Karnataka (IN); Li Ou, Bangalore Karnataka (IN); Nagaraju Konduru, Bangalore Karnataka (IN)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 343 days.

(21) Appl. No.: 16/316,297

(22) PCT Filed: Jun. 22, 2017

(86) PCT No.: PCT/EP2017/065350
§ 371 (c)(1),
(2) Date: Jan. 8, 2019

(87) PCT Pub. No.: WO2018/010929
PCT Pub. Date: Jan. 18, 2018

(65) Prior Publication Data
US 2020/0181560 A1    Jun. 11, 2020

(30) Foreign Application Priority Data

Jul. 12, 2016  (IN) .............................. 201611023831

(51) Int. Cl.
  *C12M 1/34* (2006.01)
  *C12M 3/06* (2006.01)
  *C12M 1/36* (2006.01)
(52) U.S. Cl.
  CPC ............ *C12M 41/46* (2013.01); *C12M 23/16* (2013.01); *C12M 27/16* (2013.01); *C12M 41/36* (2013.01); *C12M 41/48* (2013.01)
(58) Field of Classification Search
  CPC ...... C12M 23/16; C12M 27/16; C12M 41/36; C12M 41/46; C12M 41/48
  See application file for complete search history.

(56) References Cited

U.S. PATENT DOCUMENTS

2005/0272146 A1   12/2005  Hodge et al.
2011/0162439 A1   7/2011   Ayliffe
(Continued)

OTHER PUBLICATIONS

PCT International Search Report and Written Opinion for PCT Application No. PCT/EP2017/065350 dated Sep. 7, 2017 (9 pages).

*Primary Examiner* — Lydia Edwards
(74) *Attorney, Agent, or Firm* — Eversheds Sutherland (US) LLP

(57) ABSTRACT

A microfluidic device (100) is disclosed for in-process monitoring of cell culture conditions including for example one or more of: cell density; cell viability; secreted proteins; protein analysis; epitope markers; concentrations of metabolites or nutrients and antigenic determinations; the device comprising: a cell inlet path (120); plural fluid reservoirs (130) in fluid communication with the cell input path, a cell analysis area (160) in fluid communication with the path and reservoirs, and a waste storage volume (166) also in fluid communication with the cell analysis area, the device being operable to cause a primary fluid flow along the inlet path to the analysis area, and to selectively cause secondary fluid flow(s) into the path from none, one or more of the selected (Continued)

reservoirs to combine, if one or more of the reservoirs are selected, with the primary fluid flow from the cell inlet path, in each case for analysis at the cell analysis area, the device being further operable to cause a fluid flow of the primary and any combined secondary flows from the cell analysis area into the waste storage volume.

10 Claims, 3 Drawing Sheets

(56) References Cited

U.S. PATENT DOCUMENTS

2015/0210971 A1 7/2015 Baskar et al.
2015/0253321 A1 9/2015 Chou et al.

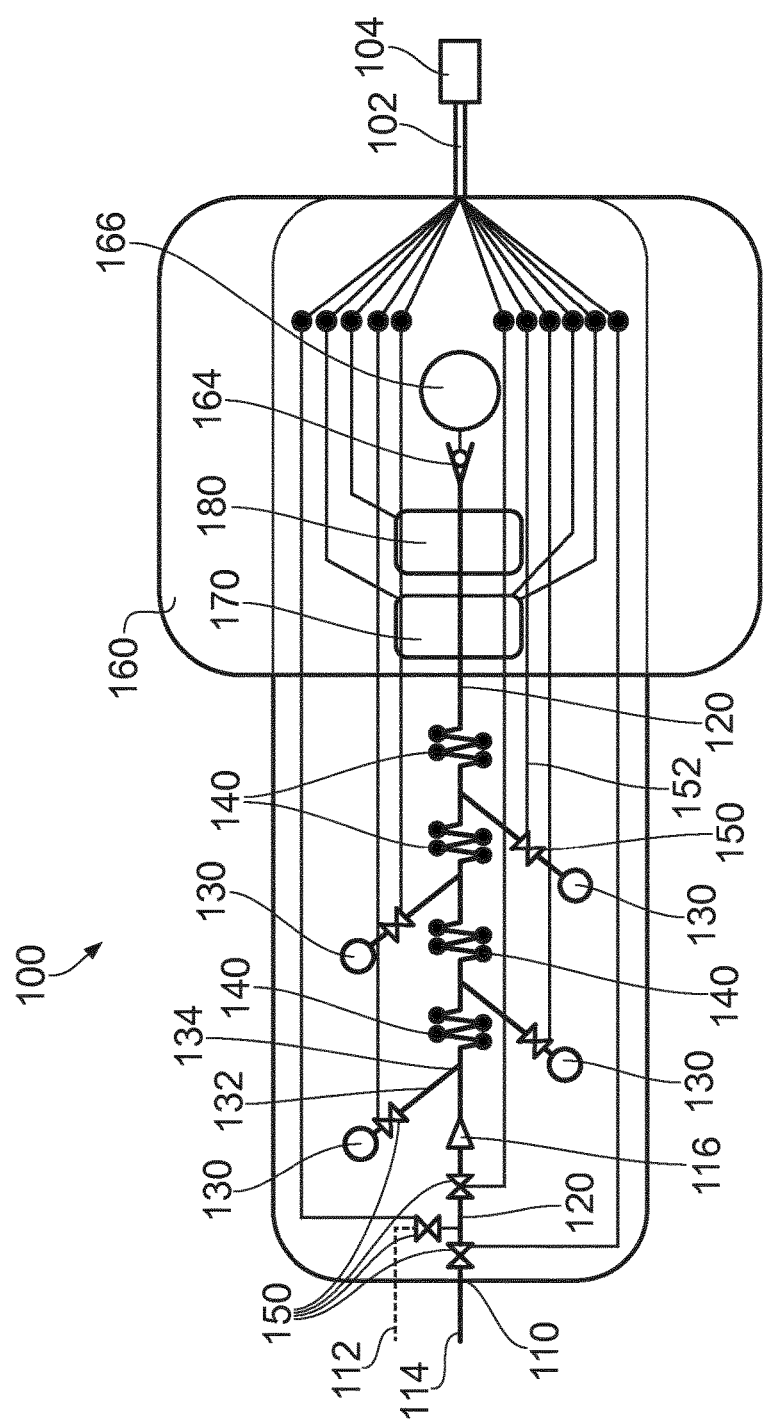
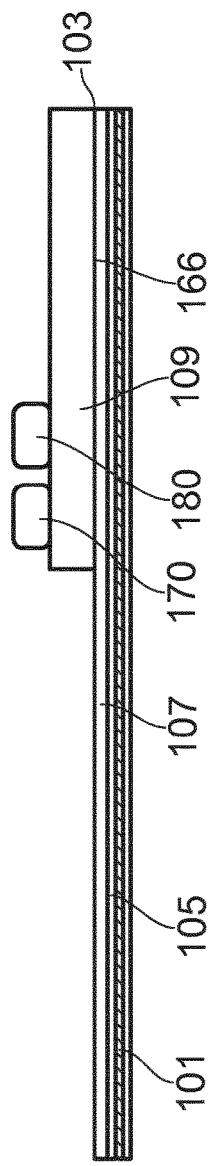
FIG. 2
FIG. 3

MICROFLUIDIC DEVICE FOR CELL CULTURE MONITORING

CROSS REFERENCE TO RELATED APPLICATIONS

This application claims the priority benefit of PCT/EP2017/065350 filed on Jun. 22, 2017 which claims priority benefit of Indian Application No. 201611023831, filed Jul. 12, 2016. The entire contents of which are hereby incorporated by reference herein.

TECHNICAL FIELD

The present invention relates to a microfluidic device for in-process monitoring of the effectiveness of multiple cell culture parameters for example in the field of immunotherapeutic cell cultivation, particularly, but not exclusively, including cell imaging.

BACKGROUND

The important parameters for cell growth, which usually mimic their in vivo state, are generally well recognised presently and for specific cells lines, for example those used to express monoclonal antibodies, their cell culture parameters can be predicted reasonably accurately, based on previous experience. Thus cell culturing, even with continuously fed batch culturing, can be readily optimised. However, where the characteristics of seed cells of a cell culture batch, for example in single batch autologous immunotherapeutic cell culture, are largely unknown, or highly variable, then to some degree, the cell culture parameters have to be adjusted based on culture sampling during the culturing process, in order to optimise that process.

Various sensors are available commercially to detect in-process cell culture parameters, for example, to detect concentrations of $CO_2$, $O_2$ and $N_2$ gases, and temperature, and these can be used to provide known satisfactory culture conditions. However, for unknown cell characteristics, it is the resultant cell activity that is important, rather than the exact input parameters, so it is more important to monitor the effectiveness of the input parameters. Known measures of effective cell culture conditions are: cell density (over time providing an indication of cell division rates); cell viability; metabolites and nutrients, for example glucose, lactate, and ammonium concentrations; expression of certain proteins (for example to determine the ratio of killer and helper T cells and determine functionally active cells); and antigenic determinants (development of epitopes).

Whilst it is known to monitor these cell conditions, conventionally, their monitoring involves taking a sample from the cell culture and examining the sample under a microscope at the laboratory workbench, for example as described in U.S. Pat. No. 73,696,969, or using colorimetric, fluorometric or spectroscopic analysis of samples. Each time a sample is taken, there is a risk of contaminating the cell culture. It is vitally important in immunotherapy that no, or few, pathogens are administered to a patient, and so reducing the risk of contamination during cell culture is very important. More frequent monitoring with fewer steps, and automatic corrective alterations in the cell culture inputs provide a better chance of producing effective therapeutic cell cultures, in less time than would be possible with conventional multi-condition determination. This is particularly import for sensitive stem cell culturing.

Further, the inventors have realised that to avoid contamination risks multiple conditions for example as mentioned above could be monitored by a single disposable monitor used in-process, i.e. in situ during cell culture, thus avoiding the need to sterilise used components.

The problems mentioned above are addressed by embodiments of the invention described and illustrated herein, which fall within the ambit of the claims herein.

SUMMARY OF THE INVENTION

Aspects of the invention are set out in the independent claims herein, with preferred features set out in dependent claims.

More advantages and benefits of the present invention will become readily apparent to persons skilled in the art in view of the detailed description below. Whilst the invention is presently characterised by the claims, the invention may extend to any combination of features described herein, not necessarily those features claimed. Further, the invention may be defined by only a fraction of the features in any one claim combined with the whole, or a fraction of the features from one or more other claims.

DRAWINGS

The invention will now be described in more detail with reference to the appended drawings, wherein:

FIG. 2 shows schematically a plan view of the microfluidic device shown in FIG. 1;

FIG. 3 shows a side view of the microfluidic device shown in FIG. 2;

DETAILED DESCRIPTION

Figure 1:
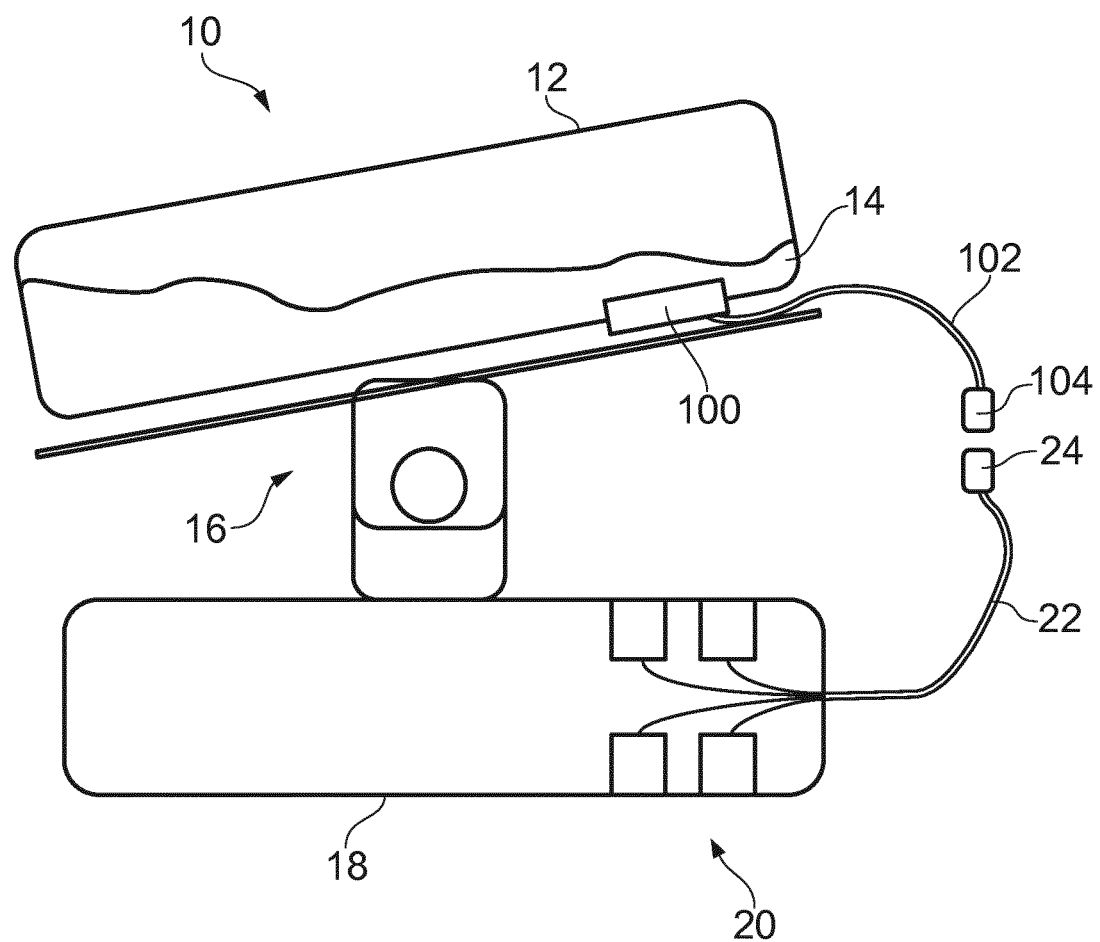
FIG. 1 shows schematically cell culture apparatus employing an in process-cell culture monitoring microfluidic device.

FIG. 1 shows cell culture apparatus 10, in this case comprising: a cell culture vessel 12, in this embodiment formed from a flexible bag, a cell culture mix 14, which is, depending on the length of cell culture, a mixture of mammalian cells which have a tendency to clump together, and liquid cell culture media, including known cell growth media. The apparatus 10 further includes a rocking platform 16 which gently mixes the cell mixture 14 while rocking. The platform 16 is supported on a base 18.

The cell culture mix 14 is monitored periodically by the microfluidic device 100, which in this case is attached to the outside of the bag 12, and has an inlet, described in more detail below, in fluid communication with the interior of the bag 12 and the cell culture mix 14. The device 100 further includes an umbilical 102 which includes in this embodiment an electrical power supply, signal lines (electrical and/or optical fibre), and pneumatic feeds for valve operation.

The base 18 includes a complementary a microcontroller and associated hardware 20 for controlling the electrical supply to the device, as well as a data input for information coming for the device, and a pneumatic supply controller, all connected to the device 100 via a complementary umbilical 22, and a complementary connector 24 which mates with a complementary connector 104 on the end of the device's umbilical 102. In summary, the microcontroller is used to control the functioning of the device, and to receive information from the device. Whilst the microcontroller and its associated hardware 20 are preferably located in the base 18, they may be located elsewhere. The complementary connectors 24/104 are used so that the device 100 can be unplugged and therefore made disposable along with the cell bag 12 once its final cell load has been used, while the microcontroller and associated hardware 20 are reusable together with the platform 16.

FIG. 2 shows the micro fluidic device 100 in more detail. The device 100 is of a layered construction and includes a cell culture mix inlet 110, which leads to an inlet fluid path 120. Branched from the inlet path 120 are plural, four in this case, fluid reservoirs 130. Each reservoir has a reservoir fluid path 132 teeing into the inlet fluid path 120 at a respective reservoir fluid entry 134 point, only one of which is referenced in the drawings for conciseness. Downstream of each reservoir fluid entry 134 point is a mixing arrangement 140, described below in more detail. In each fluid path there is a pneumatically operated valve 150, only some of which are referenced for conciseness. The pneumatic values 150 are operable by means of gas ducts 152, only one of which is referenced, extending from each valve to the umbilical 102. Essentially, these valves are diaphragms where pneumatic pressure squeezes the fluid path shut to restrict flow in the respective path and the pressure is released to open the valve, all controlled by the controller 20. This action provides a valve function and also with the aid of additional non return valves, described below, provides fluid flow. The device further includes a wash fluid inlet path 112 and an inlet cell de-clumping arrangement 114, described in more detail below, each upstream of the reservoir fluid entries 134.

In order to produce a flow in the inlet path a non-return valve 116 is located downstream of the initial pneumatic valves 150. Cyclic operation of these initial valves causes a small mass movement of liquid the inlet path 120, which moves away from the values, including a small volume of liquid which moves past the one way valve 116 toward the analysis area. Since the flow cannot return, the cyclic closing of the valves produces said flow in pulses.

Downstream of the reservoir fluid entries 134 is an analysis area 160 which includes a cell imager 170, in this case a miniature CMOS microscope, and a spectrophotometer 180 comprising a light detector for measuring light absorbance, both available commercially, the microscope and spectrophotometer being controlled by the microcontroller 20 via the umbilical 102. The microscope and spectrophotometer share a common light source provided by an optical fibre from the umbilical 102. Various spectroscopic cell culture analysers can be employed, for example: impedance based spectroscopy can be used to measure cell viability and, cell density; and Raman, Near IR, Medium IR, Far IR and other light-based spectroscopy can be used to measure metabolite and nutrient concentration. Cell culture imagers such as fluorescence microscopy, coloured and/or monochromatic light based microscopy, digital holography, differential interference microscopy, confocal microscopy etc. can be used to measure epitope proteins, secreted proteins including protein analysis.

Downstream of the analysis area 160 is a waste non return valve 164 and a waste reservoir 166, in this case a flexible walled reservoir which expands to accept waste fluids from the analysis area 160. Operation of the valves 150 which are downstream of the inlet non return valve 114, produce a small flow in a respective reservoir fluid path 132 toward the analysis area by virtue of the waste non-return valve 164, in a similar manner to the flow generated with respect to the inlet non return valve 114.

FIG. 3 shows the general construction of the device 100 as a side view. The device has a layered construction, starting with a base substrate 101, in this case formed from a thermoset plastics material. On top of that is an intermediate layer 105 which includes etched pneumatic paths for supplying gas pressure to respective valves 150. On top of layer 105 is a further layer 107 including multiple components including a membrane for the valves 150, etched tracks for the cell culture fluid paths, etched reservoir volumes and reservoir paths, as well as the reed type elements for the non-return valves 114 and 164, and a volume for the waste storage volume 166 which acts together with a portion of the flexible membrane to form a flexible walled waste receptacle which expands to accept waste but needs no vent. On top of the layer 107 is a transparent layer 109, to which is mounted the microscope 170 and the spectrophotometer 180 thus light from the analysis area can propagate to those components. An umbilical connector 103 provides the necessary commination and power routes.

Figure 4:
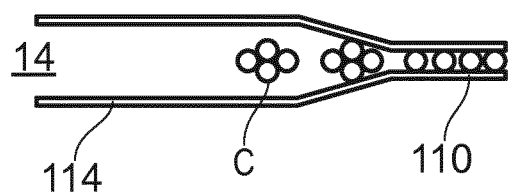
FIGS. 4, 5, 6 and 7 show views of elements of the microfluidic device shown in FIGS. 2 and 3.

FIG. 4 shows one embodiment of a cell de-dumper or cell separator 114, which employs a tapering pathway which breaks down the cell clumps C into single or small clumps, for onward passage into the inlet 110, for subsequent analysis. FIG. 4 demonstrates the generally small capillary size of the cell inlet 110, which whilst shown as having about the width of a cell, may be larger.

Figure 5:
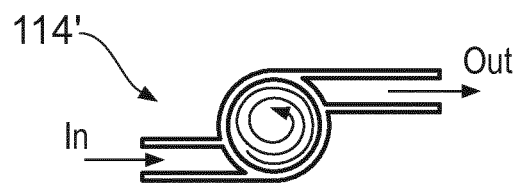
Figure 6:
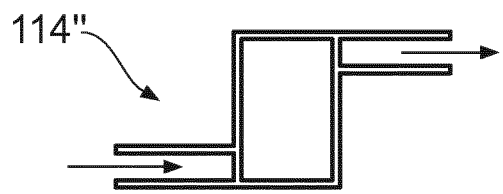

FIGS. 5 and 6 show alternative cell separators 114' and 114", each employing a circuitous turbulent flow path to impart flow shear forces into cell clumps to gently break up the clumps ready for subsequent analysis.

Figure 7:
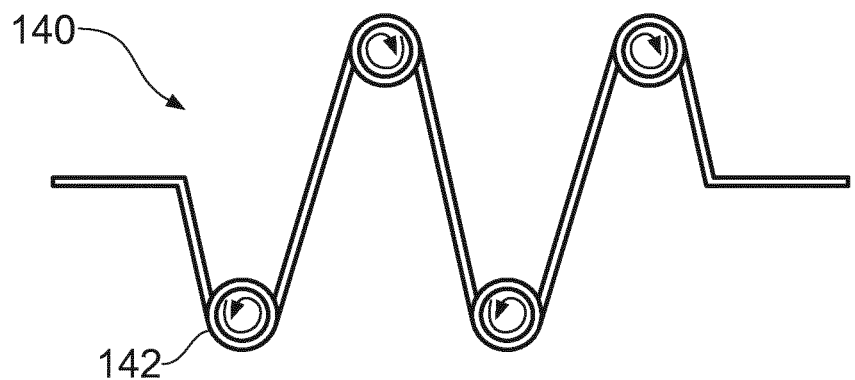

FIG. 7 shows an enlarged view of the mixing arrangement 140. The arrangement 140 includes sudden changes in the direction 142 of the inlet fluid path 120, four changes in direction in this case, all at greater than 90 degrees of turn.

In operation the controller 20 operates associated hardware to cyclically operate the initial pneumatic valves 150 in order to draw cell culture mix 14 into the inlet 114 where cell clumps are broken into single cells or small clumps. The cells are drawn into the inlet path 120 and on to the analysis area where the number of cells can be counted at the cell imager to determine cell density. Alternatively, or as well as, the spectrophotometric properties of the cells or cell culture can be determined at the spectrophotometer, thus cell metabolites, nutrient concentrations and secreted proteins can be determined. As well as this, or alternatively, the controller can open one or more of the valves 150 in the reservoir fluid paths 132 to allow aliquots of the contents of one or more of the reservoirs 130 to mix selectively with the contents of the inlet path 120 reservoir at a respective mixing arrangement 140. Thus cell markers can be introduced to mark cells so that cell viability or epitopes can be recognised at the imager. It will be understood that the above are merely examples of the type of monitoring and determinations which can be achieved with the device described above.

Analysed products are then caused to flow into the waste storage volume 160 according to the method described above. If necessary, a washing fluid can be introduced from the wash fluid inlet 112 to cleanse the inlet fluid path and the analysis area. The wash fluid reservoir is, in this instance not part of the device 100, but is a separate fluid supply, for example part of the liquid supply to the cell culture vessel 12.

The monitoring and determination according to the above technique can be repeated multiple times until the reservoir 130 contents are exhausted, although in practice there will be sufficient reservoir contents to supply separate aliquots for a complete cell culture process—start to finish, the process being monitored by the device and its determinations used to feedback to the controller which can adjust the parameters of the cell culture, for example increasing or decreasing nutrient supply or perfusion rates and determining when the viable cell density has reach the desired levels.

The invention is not to be seen as limited by the embodiments described above, but can be varied within the scope of the appended claims as is readily apparent to the person skilled in the art. For instance, the microfluidic device described herein is intended to perform periodic monitoring by ingestion of small amounts of cell culture mix i.e. as low as just a few µl to of cell culture mix 14 for analysis (as described above), which is a significantly low percentage of initial starting cell culture volumes of 50 ml or less, which is often the case where autologous immunotherapy is practiced. However, each cycle may additionally require several cell culture analyses, various reagents from the reservoirs, as well as a wash cycles between each analysis, meaning that each monitoring sequence will require a fluid throughput of around 1 ml. However, the invention is applicable to larger volumes of up to about 2 or 3 ml of throughput in each cycle. Three sequences a day over say a fourteen day period could be employed by the end user, thus the waste reservoir 166 should be capable of accepting 50-150 ml or so of fluid.

Unidirectional fluid flow is described as being generated by one way valves and cyclic operation of diaphragm type valves to cause a flow. However, other flow generators would be readily apparent to a skilled addressee, for example the waste reservoir could be made to expand on command for example using a pneumatically powered piston which would draw in fluid from the inlet 110 and any opened reservoir fluid paths 132. Alternatively, capillary action could be used as a means of generating fluid flow. Conventional pumps could be used also. The valves shown could be replaced or supplemented with other known valves.

The microscope 170 and spectrophotometer 180 are located at the cell analysis area, however additional analysis devices can be used, for example impedance electrodes can be disposed on either side of the path that runs through the analysis area to measure impedance of the cell culture mix. Other known cell culture analysers could be employed also.

The invention claimed is:

1. A microfluidic device for in-process monitoring of cell culture conditions including one or more of: cell density; cell viability; secreted proteins; protein analysis; epitope markers; concentrations of metabolites or nutrients and antigenic determinations; the device comprising:
   a cell inlet path;
   plural fluid reservoirs in fluid communication with and branched from the cell inlet path;
   a cell analysis area in fluid communication with said cell inlet path and plural fluid reservoirs; and
   a waste storage volume in fluid communication with the cell analysis area,
   wherein the device is operable to cause a primary fluid flow along the cell inlet path to the cell analysis area, and to selectively cause secondary fluid flow(s) into the cell inlet path from one or more of the plural fluid reservoirs to combine with the primary fluid flow from the cell inlet path, in each case for analysis at the cell analysis area,
   wherein the device is further operable to cause a fluid flow of the primary and combined secondary flows from the cell analysis area into the waste storage volume, and
   wherein the cell analysis area includes multiple cell culture analysers for determining multiple said cell culture conditions, and
   wherein the cell inlet path includes a means for separating cell clumps into single cells or smaller clumps of cells, by means of one or more of a tapering inlet passage or a passage arranged for turbulent flow of cell clumps entrained in the flow.

2. A device according to claim 1, wherein the device further includes a washing fluid path and is operable further to cause flow in the washing fluid path to flow through at least a portion of the cell inlet path which is upstream of the reservoirs, and on to the analysis area and into the waste storage volume, to provide cleansing.

3. A device according to claim 1, wherein the cell analysis area includes one or more of: a cell imager, and/or a spectroscope, and/or a pair of cell impedance measuring electrodes.

4. A device according to claim 3, wherein when both the imager and spectroscope are employed, a single light source is shared by the cell imager and spectroscope.

5. A device according to claim 1, wherein the cell inlet path includes a mixing arrangement.

6. A device according to claim 1, wherein fluid flow is generated by means of compressing the inlet path and one or more one way valves which allow such compressed fluid to move in one direction only along the path toward the analysis area.

7. Cell cultivation apparatus comprising a cell culture vessel supported on a rockable table, the vessel having within it, or attached thereto a microfluidic device according to claim 1, in cell culture fluid communication with the vessel, and an umbilical connecting the device to an associated controller and hardware.

8. The device according to claim 5, further comprising a plurality of mixing arrangements, the plurality of mixing arrangements comprising the mixing arrangement, each respective mixing arrangement of the plurality of mixing arrangements being downstream of a respective point at which a respective secondary fluid flow of the secondary fluid flows enters the inlet path.

9. A method for in-process monitoring of cell culture conditions including one or more of: cell density; cell viability; secreted proteins; protein analysis; epitope markers; concentrations of metabolites or nutrients and antigenic determinations, the method comprising the steps, in any suitable order, of:
   providing a microfluidic device having: a cell inlet path; plural fluid reservoirs in fluid communication with and branched from the cell input path, a cell analysis area in fluid communication with the cell inlet path and plural fluid reservoirs, and a waste storage volume in fluid communication with the cell analysis area, the cell analysis area including multiple cell culture analysers for determining multiple said cell culture conditions, wherein the cell analysis area includes multiple cell culture analysers for determining multiple said cell culture conditions, and wherein the cell inlet path includes a means for separating cell clumps into single cells or smaller clumps of cells, by means of one or more of a tapering inlet passage or a passage arranged for turbulent flow of cell clumps entrained in the flow;
   operating the device to cause a primary fluid flow along the inlet path to the analysis area, and to selectively cause secondary fluid flow(s) into the path from one or more of the selected reservoirs to combine with the primary fluid flow from the cell inlet path, in each case for analysis at the cell analysis area, and further operating the device to cause a fluid flow of the primary and any combined secondary flows from the cell analysis area into the waste storage volume.

10. The method of claim 9 further comprising the steps of:

analysing the fluid at the analysis area by one or more of microscopy, fluorescence microscopy, coloured and/or monochromatic light based microscopy, digital holography, differential interference microscopy, confocal microscopy or spectrophotometry impedance based, Raman, Near IR, Medium IR, Far IR spectroscopy; and electrical impedance.

* * * * *